United States Patent [19]

Long et al.

[11] Patent Number: 5,320,620

[45] Date of Patent: Jun. 14, 1994

[54] LASER SURGICAL DEVICE WITH BLUNT FLAT-SIDED ENERGY-DELIVERY ELEMENT

[75] Inventors: Gary Long, Cincinnati; Arnold H. Deutchman, Columbus, both of Ohio

[73] Assignee: Laser Centers of America, Cincinnati, Ohio

[21] Appl. No.: 723,984

[22] Filed: Jul. 1, 1991

[51] Int. Cl.$^5$ .................................. A61N 5/06
[52] U.S. Cl. ............................ 606/28; 606/2; 606/16
[58] Field of Search ................. 128/395, 397–400; 606/2–18, 26, 27

[56] References Cited

U.S. PATENT DOCUMENTS

| | | | |
|---|---|---|---|
| 4,126,136 | 11/1978 | Auth et al. | 606/15 |
| 4,209,017 | 6/1980 | Shaw | 606/28 |
| 4,273,127 | 6/1981 | Auth et al. | 606/3 |
| 4,627,435 | 12/1986 | Hoskin | 606/17 |
| 4,693,244 | 9/1987 | Daikuzono | 606/15 |
| 4,736,743 | 4/1988 | Daikuzono | 606/15 |
| 4,773,413 | 9/1988 | Hussein et al. | 606/28 |
| 4,832,979 | 5/1989 | Hoshino | 606/28 |
| 4,878,725 | 11/1989 | Hessel et al. | 606/7 |
| 4,992,298 | 2/1991 | Deutchman et al. | 427/38 |
| 4,994,060 | 2/1991 | Rink et al. | 606/28 |

FOREIGN PATENT DOCUMENTS

| | | | |
|---|---|---|---|
| 406454 | 1/1991 | European Pat. Off. | 606/2 |
| 467459 | 1/1992 | European Pat. Off. | 606/7 |
| 3720742 | 1/1988 | Fed. Rep. of Germany | 128/395 |
| 2076993 | 12/1981 | United Kingdom | 606/15 |

OTHER PUBLICATIONS

Informational material entitled "Ion Implantation (Advanced Technologies for Surface Engineering)", from BeamAlloy Corporation of Dublin, Ohio.
Informational literature entitled "Surface Engineering-R and D Services," from BeamAlloy Corporation of Dublin, Ohio.
Article entitled "Ion Nitriding and Nitrogen Ion Implantation: Process Characteristics and Comparisons", by Deutchman et al., Industrial Heating, Jan. 1990, pp. 32–35.
Article entitled "Practical Applications of Ion Beam Mixing: A New Surface Treatment Technique", by Deutchman et al., Industrial Heating, Feb. 1988, pp. 30 and 31.
Article entitled "Deposition–A Gem of a Process", by Deutchman et al., Advanced Materials and Processes Jun. 1989, pp. 29–33.
Article entitled "Application and Utilit of Industrial Diamond-Like Films", by Deutchman et al., Industrial Heating, Jul. 1988, pp. 12–14.

*Primary Examiner*—David M. Shay
*Attorney, Agent, or Firm*—Lowe, Price, LeBlanc & Becker

[57] ABSTRACT

A laser light energy powered device for providing directed emission of laser light energy has a blunt, i.e., non-sharp, laser light emitting tip element. The tip element is preferably formed as a slab defined by two pairs of parallel sides, a proximal end face for receiving laser light energy conveyed thereto through an optic fiber, and a laser light energy emitting curved-sided distal end surface. The curved side surface is contiguous at one end with one of the elongate parallel sides defining the tip element. All surfaces are smooth and polished in one embodiment and laser light energy is emitted therefrom in a first portion focused generally forwardly of the distal end of the tip element and in a second portion emitted laterally of the end portion of the tip element. In other aspects of the invention, the distal end surface portions of the tip element are provided with a smooth thin layer of a high temperature melting point material ballistically bonded to the tip element material by an ion beam mixing process or an ion beam enhanced deposition process with sufficient energy to form a secure metallic-ceramic bond with the material of the tip element. This securely bonded layer totally absorbs all laser light energy reaching it through the tip element material and converts it into heat applicable by contact with tissue for surgical purposes.

30 Claims, 4 Drawing Sheets

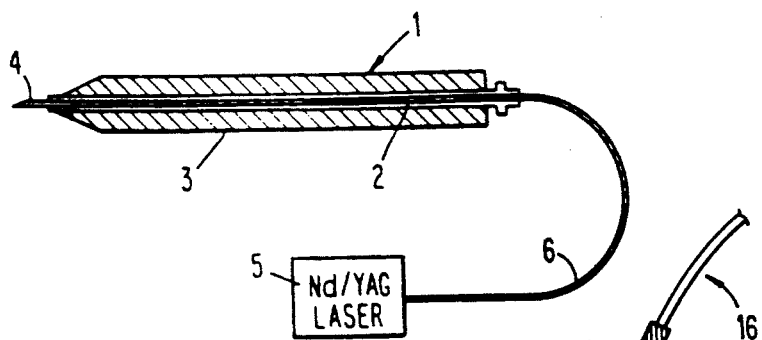
FIG. 1
PRIOR ART
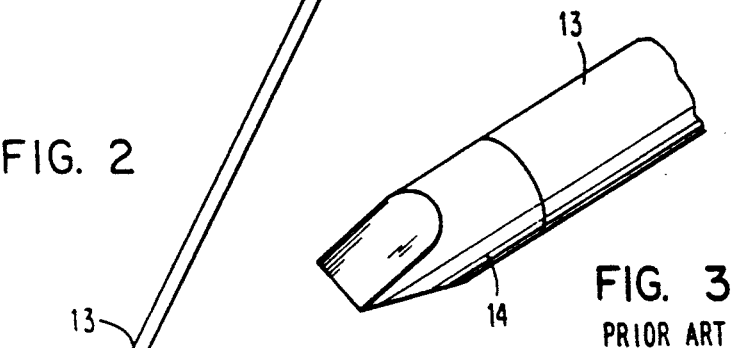
FIG. 2
FIG. 3
PRIOR ART
FIG. 4
PRIOR ART
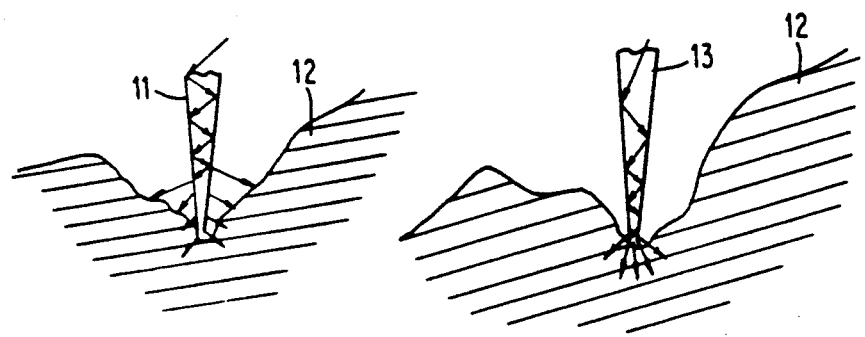
FIG. 5
PRIOR ART
FIG. 6
PRIOR ART

LASER SURGICAL DEVICE WITH BLUNT FLAT-SIDED ENERGY-DELIVERY ELEMENT

FIELD OF THE INVENTION

This invention relates to a device for delivering laser energy for localized applications, and more particularly to such a device for controllably delivering energy from a laser energy source through an unsharpened, flat-sided, energy-delivery element to perform surgical functions such as incision, cauterization and coagulation.

BACKGROUND OF THE PRIOR ART

Known laser surgical devices, many of which are applied by direct contact with tissue to be affected thereby, often utilize emitted laser light energy for ablation or vaporization of tissue. Laser light energy is also sometimes used as a supplement with an otherwise traditional scalpel-type sharp-edged cutting implement. An example of such a device is disclosed in U.S. Pat. No. 4,126,136, to Auth et al. This photocoagulating scalpel system includes a scalpel having a physically sharp transparent blade for forming 20 an incision, with a laser energy source optically coupled to the blade through a low-loss fiber optic wave guide. Laser light is emitted through the sharp edge of the blade for coagulating blood adjacent the incision. The material used for such a sharp scalpel blade is quite hard, but the required sharpness may be difficult to maintain.

Another recently-proposed device is described in U.S. Pat. No. 4,627,435, to Noskin, in which a surgical knife includes a handle supporting a diamond blade coupled to a Nd/YAG laser. See FIG. 1 hereof. The surgical diamond knife 1 has a handle 3 supporting a diamond blade 4 connected to the Nd/YAG laser 5 by optical fibers 6. FIG. 2 illustrates another embodiment of the same invention, wherein a relatively long slim handle 13 houses an optical fiber bundle (not shown) coupled at one end to a wedge-shaped diamond blade 14. The cylindrical body portion 13 of this knife is connected at a proximal end to a sheath 16 which protects the bulk of the length of the optical fiber. See FIGS. 3 and 4 for Hoskin's shapes for laser energy delivering diamond tips 14 and 24. In each case, the laser energy-delivering diamond tip element has a sharp edge. Laser light provided to such tip elements is internally reflected through the body of the tip element from the optic fiber to the cutting edge to enable the surgeon to more readily make his incisions.

In yet another example of the art, U.S. Pat. No. 4,693,244, to Daikuzono, teaches a medical and surgical laser probe in which laser energy from an optical fiber is conveyed by internal reflection within tapered tip elements 11 (in FIG. 5), or 13 (in FIG. 6) to specifically formed energy-delivery zones at their frontal pointed ends. When certain geometric parameters are satisfied, laser energy can leak out from the tapered side faces of rod member 11 to reach tissue 12, as depicted in FIG. 5, so that the flow of laser energy density emitted from the narrow tip end face is lowered. This would make incision of the tissue 12 difficult. Also, the laser energy which leaks from the tapered face irradiates tissue at a distance and this may be undesirable. However, when the refractive index of the tip element and its geometry both satisfy conditions specified in this reference, a much higher energy density is attainable at the tip end which is shaped and treated to deliver thermal energy generated by partial absorption of the laser light energy in a thin coating, with another portion of the available laser light energy emitted through the tip end.

In devices of the type discussed hereinabove, there are various inherent structural and operational limitations encountered by a user, e.g., that the laser energy delivery end must be maintained physically sharp. Furthermore, since the energy is delivered through a very small volume of the tip element at the sharp edge or pointed tip, the surgeon/user must exercise extreme care in controlling the rate at which laser energy is being delivered as he or she performs a variety of inter-related functions, i.e., makes incisions, cauterizes cut blood vessels, and coagulates leaked-out blood so that it does not interfere with accurate viewing of or access to the surgical site.

There is, accordingly, a need for a sturdy, blunt, i.e., physically non-sharpened, tip element by which laser light energy can be utilized precisely to selectively perform incisions, to cauterize blood vessels, and to coagulate blood.

SUMMARY OF THE DISCLOSURE

It is a principal object of this invention to provide a blunt, flat-sided laser energy delivery tip element, i.e., one free of physically sharp cutting edges, which is suitable for use in a hand-held surgical tool receiving laser energy via an attached optic fiber.

It is a further object of this invention to provide a blunt, flat-sided laser energy delivery tip element for performing a variety of surgical functions.

It is a further related object of this invention to provide a surgical tool which may be simply operated by a surgeon, trained in and utilizing conventional laser surgical techniques, to selectively perform with just that single tool a variety of surgical procedures such as incisions, cauterization of incised blood vessels, and coagulation of leaking blood at a surgical operation site.

In another aspect of this invention, there is provided a process for treating an end surface of a blunt, slab-shaped laser energy delivery tip element with which a surgeon employing conventional laser surgical techniques can readily and controllably perform incisions, cauterize incised blood vessels, and ablate or vaporize tissue and coagulate blood.

These and other related objects of the present invention are realized by providing a heating device powered by laser light energy, which has a laser energy delivery tip element formed of a laser light transmitting first material. The tip element is defined by a pair of planar parallel geometrically similar elongate outer faces, a planar proximal end face normal to the pair of similar outer faces, a long narrow rectangular planar side face normal to the pair of outer faces and to the proximal end face, a short narrow rectangular planar side face of a length shorter than the long side face and oriented parallel thereto, and a curved distal end face contiguous with the shorter side face at one end and intersecting the long side face at a blunt distal end of the tip element. All of said faces are smooth and polished. The device also includes means for providing a laser light energy input to the proximal end face of the tip element, whereby a first portion of the laser light energy input is transmitted through the first material of the tip element along a length thereof and is emitted from the curved end face in a focused manner forwardly of the distal end of the tip element.

In yet another aspect of the invention, there is provided a process for preparing a contactable heating surface of a blunt light-energy receiving laser tip element, comprising the step of incorporating into a selected surface portion of the tip element a high temperature melting point material, ballistically alloyed to the material of the tip element by either an ion beam mixing process or an ion beam enhanced deposition process, to totally absorb all laser light energy conveyed thereto through the tip element material.

BRIEF DESCRIPTION OF DRAWINGS

FIGS. 1-4 relate to known structures for laser surgical devices as disclosed in U.S. Pat. No. 4,627,435, to Hoskin, titled "Surgical Knives".

FIGS. 5 and 6 illustrate known taper-sided laser energy delivery tip elements as disclosed in U.S. Pat. No. 4,693,244, to Daikuzono, titled "Medical and Surgical Laser Probe".

DETAILED DESCRIPTION OF THE PREFERRED EMBODIMENTS

A surgeon employing a laser surgical device typically holds a lightweight end-piece into which is fitted a slim elongate assembly having a tip element at a distal end. Laser energy conveyed from a laser energy source is thus actually applied to tissues of a surgical patient by the surgeon holding the tip element very close to or in actual physical contact with tissues that are to be cut, ablated, vaporized, cauterized or coagulated.

Figure 7:
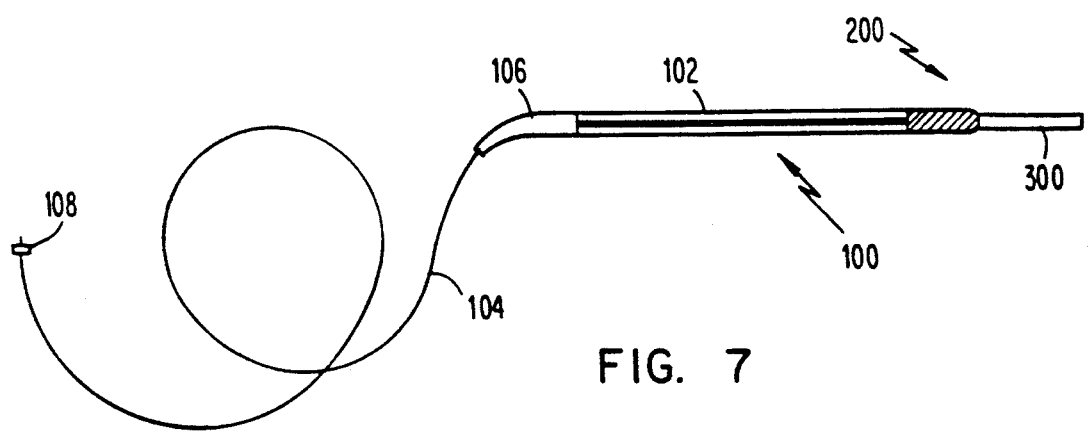
FIG. 7 schematically illustrates elements of an exemplary apparatus by which laser light energy received from a laser energy source is conveyed to a blunt, flat-sided laser light emitting tip element for surgical procedures, according to a preferred embodiment of the present invention.

As best understood with reference to FIG. 7, the principal elements of such a hand-held assembly 100 include a slim elongate body 102 connected at a proximal end to a flexible element 104 at a junction 106. Flexible element 104 comprises an outer tubular sheath protectively containing a length of an optic fiber connected by a junction 108 at one end to a source of laser energy (not shown). By such a generally well-known arrangement, laser light energy of selected wavelength is conveyed from a laser source located at a distance from the patient, by internal reflection within the optic fiber, through elongate body 102 through a delivery end 200 to the proximal end of a tip element 300.

Figure 8:
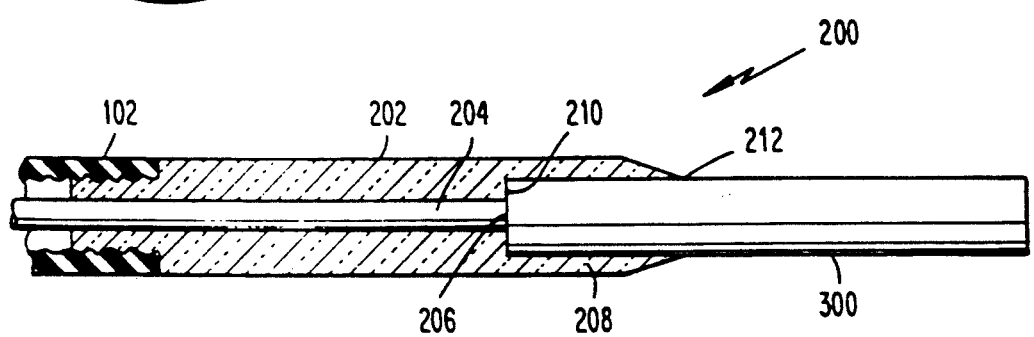
FIG. 8 is a partially-sectioned enlarged longitudinal view illustrating details at the tip end of the apparatus of FIG. 7.

As best understood with reference to FIG. 8, delivery end 200 of the device, located at a forward end of elongate element 102, is connected in known fashion to a fiber/tip connector 202 which is preferably made of stainless steel or other readily sterilizable material. An optic fiber 204 is passed into fiber/tip connector 202 so that laser light energy conveyed by internal reflection through optic fiber 204 is delivered through an end face 206 of the optic fiber.

The forward end of fiber/tip connector 202 is formed with a recess 208 into which is received the proximal end of a tip element 300. A suitable clear epoxy glue, e.g., EPO-TEK 301-2, is used to strongly attach the distal laser-light delivering end of optic fiber 204 inside fiber/tip connector 202 so that the laser light transmitting end face 206 of the optic fiber ends at the base of recess 208. Similar epoxy material is used sparingly to connect optic fiber 204, at its end face 206, to the adjacent proximal end face of tip element 300. The goal throughout is to ensure strong attachment of optic fiber 204 to fiber/tip connector 202 and to tip element 300 to ensure the physical integrity of the assembly and to facilitate transmittal of laser light energy into the body of tip element 300 with the smallest possible losses at the interface between optic fiber 204 and tip element 300. It will be understood that recess 208 has a base 210 to which a portion of the proximal end face of tip element 300 is epoxied. Some of the epoxy 212 will also form a strong bond between the walls of recess 208 and outside surfaces of tip element 300.

Figure 9A:
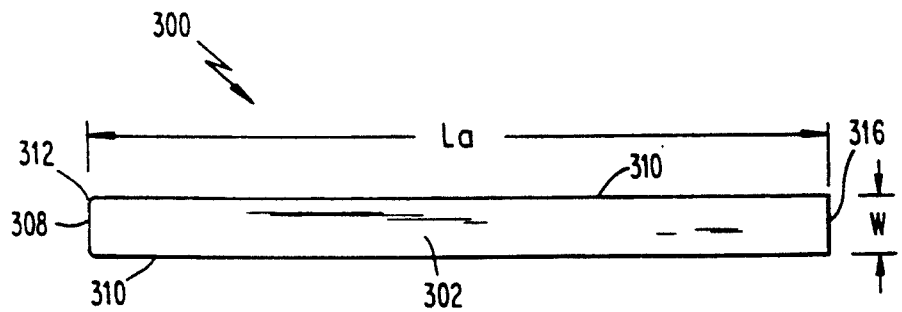
FIGS. 9A, 9B and 9C are plan, longitudinal side elevation and distal end elevation views, respectively, of a laser light emitting tip element shaped according to the preferred embodiment of this invention.
Figure 9B:
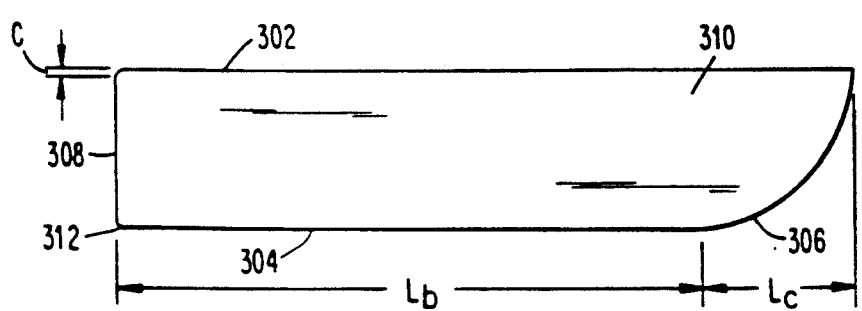
Figure 9C:
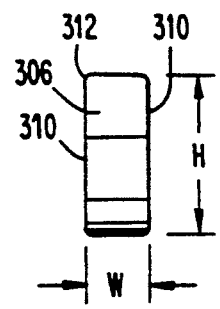

The particular advantageous geometry of the blunt, flat-sided tip element, according to a preferred embodiment of this invention, is depicted in FIGS. 9A-9C and is described hereinbelow.

As depicted in the longitudinal plan view of FIG. 9A, tip element 300 has a length $L_a$ and a width W. Similarly, as seen in the side elevational view of FIG. 9B, tip element 300 has a long rectangular upper face 302, of length $L_a$, and a somewhat shorter parallel rectangular opposite 304 of length $L_b$. Rectangular face 304, in the preferred embodiment, is contiguous at its forward end with a curved surface 306 which has a projected length $L_c$ in the plane of elongate face 304, so that: $L_a = (L_b + L_c)$. The other outer faces of tip element 300 are a proximal end face 308 and two similar relatively large planar, parallel side faces 310, 310.

As also depicted in FIGS. 9A-9C, all edges except the foremost edge 316 and the curved edges defining curved distal end surface 306 preferably are chamfered with a chamfer 312 having a transverse dimension C (best seen in FIGS. 9B and 9C).

Most important, it should be appreciated that tip element 300 has no sharp cutting edge to be utilized for applying a mechanical cutting force to tissues, i.e., tip element does not perform mechanical cutting with or without enhancement by laser energy.

As a practical matter, tip element 300 may be formed in any of various well known ways, e.g., by being cut or otherwise machined from a larger crystal of the selected material, formed in a mold, or the like. The basic initial shape is that of a flat cubical element which is then chamfered along its longest edges and at the edges of the proximal face and has material removed at its distal end as defined by curved face 306. All outside faces of the basic tip element 310 are polished smooth, for reasons discussed more fully hereinbelow. As will be readily understood by persons of ordinary skill in the art, such a tip element can be made quite small and to fairly tight dimensional tolerances relatively inexpensively. Suitable materials for forming tip element 300 include ceramic materials such as YAG, sapphire and silica. Relevant properties of the materials of interest are tabulated in Table 1 below.

TABLE 1

| Material | Melting Point (°C.) | Thermal Conductivity (W/m °C.) | Refractive Index at 1.06 μm Wavelength |
|---|---|---|---|
| Sapphire ($Al_2O_3$) | 2300 | 35 | 1.75 |
| Silica ($SiO_2$) | 1740 | 7 | 1.54 |
| YAG ($Y_3Al_5O_{12}$) | 2220 | 13 | 1.82 |

Figure 10:
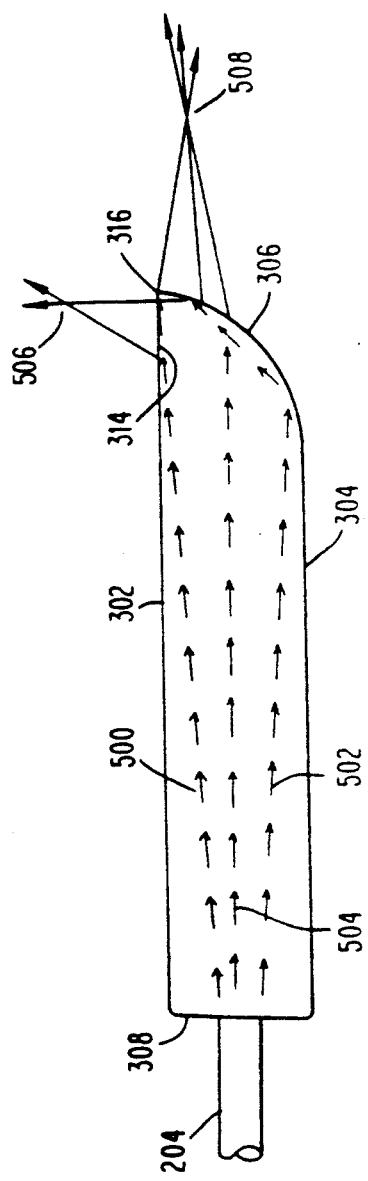
FIG. 10 is a longitudinal side elevation view, in schematic form, to illustrate paths taken by laser light emitted from the tip element of FIGS. 9A-9C.

It is believed that this simple basic "blunt", i.e., not sharp, shape ensures considerably longer durability than is possible with physically sharpened scalpel-type forms as taught, for example, in the Auth et al. reference discussed hereinabove. Furthermore, by judicious selection of the material and the shape of curved face 306, with a very simple geometry it becomes possible to deliver laser light energy both forwardly through curved face 306 and sideways through a distal end portion 314 of narrow, longitudinal face 302. This is best understood with reference to the "ray trace" illustration of FIG. 10. As depicted in FIG. 10, laser light energy conveyed by internal reflection within optic fiber 204 enters proximal end face 308 of element 300 and, possibly with some internal reflection between parallel side faces 310 separated by a width W, is transmitted toward the distal curved end surface 306 and end surface portion 314. It should be appreciated that FIG. 10 is not intended to be "to scale", but it is also to be understood that there may be some divergence of the laser light within tip element 300, as schematically depicted by the broken arrowed lines 500, 502 and 504 in FIG. 10.

Depending on the angle at which any such rays are incident on the curved smooth surface 306 they will either be internally reflected thereat (e.g., ray 502) or transmitted therethrough (e.g., ray 504). A ray may be reflected more than once (e.g., ray 502) and may be redirected to be emitted from another face of the tip element (e.g., as part of laser light emission 506 out of portion 314 of side surface 302).

Persons of ordinary skill in the art of utilizing light-transmitting materials as wave guides will appreciate that the refractive index of the material of tip element 300 typically is significantly larger than that of the ambient atmosphere as well as the refractive indices of most tissues to which tip element 300 may be contacted during use. Hence, the laser light energy will be essentially totally reflected within the material of tip element 390 at its polished faces, so long as any "ray" of the laser light is incident at such a surface of tip element 300 at an angle with respect to the local normal which is greater than a "critical angle" $\theta$. When the angle of incidence with respect to the local normal at a surface of tip element 300 is less than the value of the critical angle $\theta$, that ray of laser light will be emitted out of the tip element. This principle and the shape of curved face 306 together determine how the laser light received from optic fiber 204 into tip element 300 is eventually emitted therefrom for use.

It is with this knowledge, and to exploit this natural consequence of a change in refractive index, that this embodiment employs a blunt, i.e., non-sharp, tip element to project therefrom two flows of laser light energy. As best understood with reference to FIG. 10, the first of these flows, 506, is emitted out of end surface portion 314 and is conveniently directable by the surgeon as a laser light energy emission to treat tissue which is orthogonal to the tip surface. This first emission 506 has a relative intensity which depends on the index of the tip element material, the shape of curved face 306 and any laser light absorption at each involved surface. The other and preferably principal flow of emitted laser light energy, 508, is directed substantially forwardly of the distal end of tip element 300.

The selected dimensions for tip element 300, e.g., $L_a$, $L_b$, W, and H, the tip element material refractive index which determines the critical angle $\theta$, as well as the chosen shape for the curved end face 306, will together determine the proportions in which the laser light energy received by tip element 300 is emitted from the curved surface 306 (i.e., 508) and from the end portion 314 of the long narrow face 302 (i.e., 506).

As a practical matter, there will be a lens (not shown) intermediate the laser light energy source and a light receiving end of optic fiber 204. Depending upon the focal length of such a lens, light entering the optic fiber itself will diverge at some corresponding angle and will reflect and re-reflect along the length of optic fiber 204 to exit from the light delivery end face 206 to reach the light receiving end face 308 of the tip element 300.

Optic fibers presently are typically made of a material such as silica. Tip element 300 may, for certain applications, also be made of silica. If this is the case, then the diverging light which leaves the light delivering end surface 206 of optic fiber 204 will not experience a change in the refractive index as it is transmitted across light receiving end surface 308 into and through the length of tip element 300. On the other hand, if the tip element 30 is made of a different material, e.g., ceramic materials such as YAG, sapphire, or the like, then the different refractive index encountered by the laser light upon entry into tip element 300 will cause a further deviation. The laser light passing through such a tip element material will diverge at an angle determined in part by the input lens focal length, the refractive index of the optic fiber material, and the refractive index of the tip element material. These, obviously, are parameters which a person of ordinary skill in the art seeking to practice this invention would take into account according to well-known laws of optical physics for specific applications for the tip element 300.

As will be readily appreciated, the relative proportions of energy flows 506 and 508 can be determined by selection of the refractive index of the tip element material, the choice of tip element dimensions, e.g., $L_a$ and H, and by careful selection of the shape and specific local curvature of third face 306. Although curved face 306 is indicated in FIGS. 9B, 10 and 11B as having the profile of a quadrant of a circle, this is merely exemplary, and any smooth continuous curve may be used instead as appropriate for the task to be performed by the device. Even with presently-known materials, e.g., ceramic materials such as YAG, sapphire and silica, persons of ordinary skill in the mechanical arts can, with very little effort, readily select the refractive index, shape and dimensions to virtually "custom-tailor" such blunt, inexpensive tip elements 300 to suit a very wide variety of applications. Another factor which may be taken into account is the location of the interface between the laser light emitting end face 206 of optic fiber 204 and the laser light receiving end face 308 of tip element 300. In FIG. 10, this interface is depicted schematically as being centrally located with respect to end face 308. Clearly, it can be located upwardly or downwardly too, and this would affect the proportions 506 and 508 into which the emitted laser light energy will split.

The device can be used to project or apply energy in different ways. Thus, for example, energy from the long narrow surfaces can be used for cutting and vaporizing tissue. The power flow could then be reduced, the device turned, and energy from a broad surface used for coagulation.

Likewise, with the orthogonal flow of laser light 506, adjacent tissue could be treated without cumbersome manipulation of the tip element.

A suitable tip element for such applications could, for example, have the following physical dimensions:

$L_a = 10$ mm, $L_b = 8$ mm;
$H = 2$ mm; and a radius of curvature
$R = 2$ mm for curved surface 306
$W = 0.6$ mm.

The same basic shape as described in considerable detail in the preceding paragraphs can be utilized in yet another manner in a second embodiment comprehended within the broad scope of the present invention. The required structure, as best understood with reference to FIGS. 11A–11C, requires only the addition of a securely bonded thin laser energy absorbing layer at the surfaces defining the distal end portion of tip element 300. Specifically, the surface areas corresponding to curved surface 306, an end portion 314 of long narrow face 302, and quadrantal side surface portions of side faces 310, 310 of the previously-described embodiment are all surface-treated to create the second preferred embodiment of the present invention to realize certain other functional advantages.

Figure 11A:
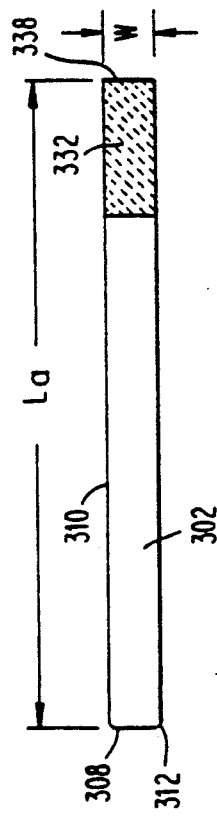
FIGS. 11A, 11B and 11C are respective plan, longitudinal side elevation and end elevation views of a second embodiment of a laser light emitting tip element shaped as depicted in FIGS. 9A-9C, wherein a distal end surface area is treated to totally absorb all laser light energy and convert it to heat.
Figure 11B:
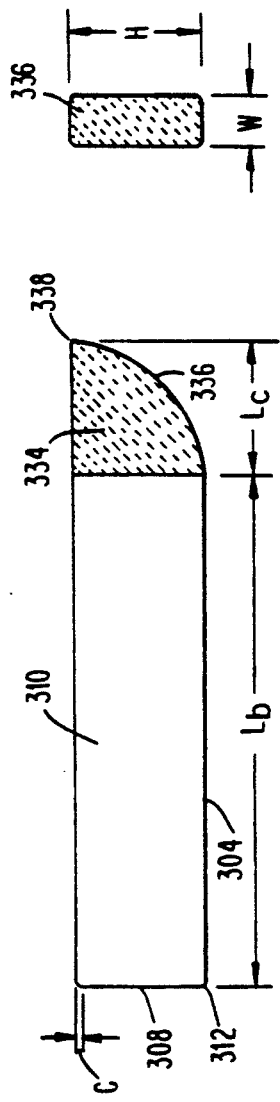
Figure 11C:
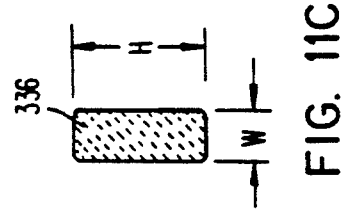

For convenience, in FIGS. 11A–11C, the layered top rectangular end surface portion is designated as 332, the adjacent layered quadrantal side end surface portions are 334, 334, and the layered curved distal end surface joining them is 336. Surfaces 332 and 336 intersect at a forward, but not sharp edge 338.

According to this second embodiment of the present invention, the desired heating layer is intended to totally absorb all laser light reaching the same through the body of tip element 300. This heating layer is preferably generated either by an ion beam mixing process or by an ion beam enhanced deposition (IBED) process. In either case, the layer comprises a high-temperature melting point material, such as a metal selected from a group of metals consisting of titanium, chromium, nickel, zirconium, molybdenum, tantalum, and tungsten, as well as metallic oxides such as yttria, zirconia and alumina. The selected constituent is "ballistically alloyed" into the material of tip element 300 at the selected surface areas, which thereby become transformed into the desired laser-energy absorbing heating surfaces. Forming such a heating layer by either an ion beam mixing process or by an ion beam enhanced deposition process leads to the formation of a very thin, uniform, securely-bonded metallic-ceramic layer to provide smooth, non-porous, tissue-contactable external surfaces. The user can then apply the treated surface portions to tissue by non-sticking contact, to thereby transmit controlled quantities of heat in a manner particularly suitable for cauterization and coagulation of body tissues and fluids. The distal end portions of the relatively large flat side faces are particularly suitable for cauterizing application of simultaneous heat and pressure.

The highly-coherent laser light beam which reaches the very thin high temperature melting point material layers at the distal end surfaces of tip element 300 is totally absorbed therein, and the laser light energy is thus entirely converted to heat in these thin surface layers. This heat is then conveniently transferred to tissue contacted by the smooth outer surface of the layer covering the distal end of tip element 300 on the layered surface areas 332, 334 and 336. It is intended that all of the laser light energy thus received internally through the material of tip element 300 at these particular surfaces be totally converted into heat.

The temperature profile of the distal end surfaces of the tip element can be controlled by the distribution of laser light and its internal reflection and/or absorption as discussed earlier. For this purpose, the thickness of the high temperature melting point material ballistically alloyed into the material of tip element 300 preferably is in the range 20 Å to 5,000 Å, and the additional thickness of the high melting point material deposited thereon preferably is in the range 5,000 Å to 200,000 Å.

Figure 12:
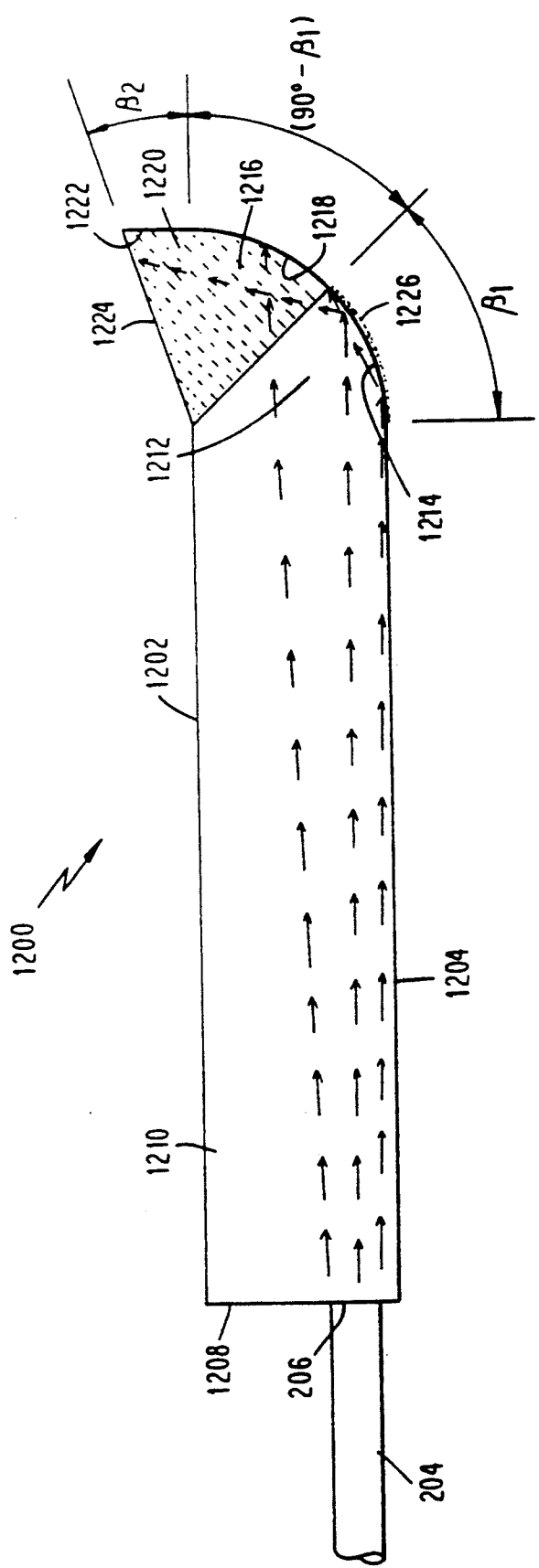
FIG. 12 is a side elevation view of a third embodiment having a laser light energy absorbing tip element.

A third embodiment 1200 of the tip element is illustrated in side elevation view in FIG. 12. This embodiment represents a variant or modification of the geometrically somewhat simpler embodiment illustrated in FIGS. 11A–11C. In the third embodiment, the laser light emitting end face 206 of optic fiber 204 is not centrally located with respect to laser light receiving proximal end face 1208 of tip element 1200. As will be readily appreciated from a comparison of FIGS. 11B and 12, significant portions of tip elements 300 and 1200 have the same basically cubical shape but the two embodiments differ at their respective distal ends.

The distal end portion of each side surface 1210, 1210 comprises: a first segment 1212 corresponding to a portion 1214 of the curved narrow end face subtending an angle $\beta_1$ and contiguous with narrow elongate side face 1204; a second segment 1216 subtending an angle $(90° - \beta_1)$ corresponding to a portion 1218 of the narrow curved end face; and a triangular segment 1220 subtending an angle $\beta_2$. This triangular segment has two edges defined, respectively, by the intersections of the planar triangular segment 1220 with a planar end face portion 1222 which is contiguous with the curved end face segment 1218 and an intersection between the triangular planar segment 1220 and a planar narrow side surface 1224, as illustrated.

In the third embodiment, the geometry of which is described in detail in the immediately-preceding paragraph, a thin light reflective layer of a metal or ceramic material 1226 is provided on only the curved end face portion 1214 to ensure internal reflection of any laser light energy incident thereon through the material of tip element 1200. No reflective layer is provided at the surfaces corresponding to quadrantal side surfaces 1212 since total internal reflection at these surfaces is readily obtained without such a reflective coating. The rest of the distal end surface, namely that corresponding to the segmental surface portions 1216, 1216, the triangular segments 1220, 1220, the curved surface 1218 and the planar faces 1222 and 1224, is provided with a ballistically bonded layer comprising a high temperature melting point material selected from a group of materials including metals such as titanium, chromium, nickel, zirconium, molybdenum, tantalum and tungsten, as well as metallic oxides such as yttria, zirconia and alumina.

Such a ballistically bonded laser light energy absorbing layer may be formed by either an ion beam mixing process or an ion beam enhanced deposition process, as discussed more fully hereinbelow.

The third embodiment per FIG. 12 differs from the second embodiment per FIGS. 11A–11C in that a portion of the curved end face is provided with a thin light refractive layer of a metal or ceramic to ensure efficient internal reflection of laser light incident thereon and a laser light energy absorbing surface which provides heated surface areas applicable to tissue by contact. The provision of heated surface portion 1224 at an angle $\beta_2$ with respect to the upper narrow side face 1202 of tip element 1200 is believed to be particularly advantageous for certain applications, e.g., for vaporization of tissues and cutting of tissues by the application of heat at the non-sharp corner defined by the intersections among planar heated surfaces 1220, 1220, 1222 and 1224.

As mentioned briefly earlier, the laser light energy absorbing material can be securely bonded to the distal end surfaces of the tip element either by ion beam mixing or by ion beam enhanced deposition. U.S. Pat. No. 4,992,298 to Deutchman et al., titled "Dual Ion Ballistic Alloying Process", discloses details of apparatus and a method for practicing an ion beam enhanced deposition process, and the relevant disclosure therein is incorporated herein by reference. Also incorporated herein by reference are the relevant portions of our contemporaneously submitted U.S. applications Ser. Nos. 07/723,987 and 07/724,019.

Apparatus and methods for practicing the ion beam mixing and the ion beam enhanced deposition (IBED) processes are commercially exploited by BeamAlloy Corporation, Dublin, Ohio. An abbreviated description of the most important aspects of forming and utilizing laser light energy absorbing layers in accordance with such known processes is provided below.

Relatively high temperatures may be expected to be generated by the absorption of laser light energy in the comparatively small volume of the laser light absorbing energy material and the material of heating element 300 or 1200 (depending on the embodiment) immediately adjacent the treated surfaces areas. Therefore, both for operational reliability and durability of the device, as well as for the patient's safety, it is important that there be no physical deterioration of the heated surface during use of the device, e.g., by delamination of the laser light energy absorbing layer from the tip element surface. According to the present invention, the desired heating layer is formed by highly energetic incorporation of the selected constituent, by either ion beam mixing or by ion beam enhanced deposition, to generate a thin, uniform, securely bonded, metallic-ceramic layer immediately adjacent the external surface of the tip element. Using either technique, as discussed in detail in the references incorporated herein by reference, an ionized plasma beam comprising high energy ions of an inert gas, e.g., neon, argon, krypton or xenon, is applied to the selected high melting point material either after an initial deposition thereof (in the ion beam mixing process) or simultaneously with such deposition (in the ion beam enhanced deposition process). In either case, the very high energy contained in the ions, transferred by impact to the high melting point material, drives the latter forcibly into the material of the tip element. The consequence is an extremely securely bonded, ballistically alloyed, very thin metallic-ceramic layer at the surface so treated.

An additional layer of the high temperature melting point material may be added thereafter, by any conventional known process after formation of the ballistically alloyed layer, following the ion beam mixing process or by continuation of the ion beam enhanced deposition process with reduced energy in the ionized plasma. These processes are discussed more extensively in our contemporaneously submitted applications (cited hereinabove) which are incorporated herein by reference for all relevant portions thereof.

The additional layer of laser light energy absorbing material is very securely attached to and, in fact, contiguous with the ballistically alloyed layer formed into the tip element surface. It may have a thickness of between 5,000 Å and 200,000 Å, with a preferred thickness of between 10,000 Å and 50,000 Å. The outermost surface of this layer will be nonporous and smooth. Upon the provision of laser light energy through optic fiber 204, and the subsequent absorption of this energy to produce heat in the ballistically alloyed layers provided as described, the user has available to him smooth, relatively large, flat heated surfaces by which coagulation of bodily fluids such as blood may be obtained. Also, although the described embodiments do not have surgically sharp cutting edges, if the thickness of the tip element is, say, of the order of 400 microns and an optic fiber of 200 microns diameter is utilized, any of the embodiments disclosed herein can provide intense heat forwardly of the distal end of the tip element to facilitate incision by vaporization and/or ablation of body tissues.

As will be appreciated from the above description of the preferred embodiments, the present invention provides a simple, inexpensive, precisely manufacturable and blunt (non-sharp tip element, by which a hand-held laser light energy powered tool can be very conveniently applied to perform a variety of surgical procedures by ablation or tissue vaporization, to effect incision, cauterization and body fluid coagulation. A variety of separate and differently shaped tools for such diverse purposes is therefore not needed, and the tip element being blunt (physically not sharp) should eliminate unintended and potentially risky incidental cuts when the laser power is turned off by the surgeon in conventional manner during the operational procedure. This should make the surgeon's task easier. Obvious extensions of the present invention to applications such as dental surgery or even sculpting of hard-to-sculpt materials such as marble can be readily visualized.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A heating device powered by laser light energy, comprising:
a laser energy delivery tip element formed of a laser light transmitting first material, said tip element being defined by a pair of planar parallel elongate outer faces both of same shape and size, a planar proximal end face normal to said pair of outer faces, a long narrow rectangular planar side face normal to said pair of outer faces and to the proximal end face, a short narrow rectangular planar side face of a length shorter than said long side face and oriented parallel thereto, and a curved distal end face contiguous with said short side face at one end and intersecting said long side face at a blunt distal end of the tip element, wherein all of said faces are smooth and polished; and means for providing a laser light energy input to said proximal end face of the tip element, whereby said laser light energy input is transmitted through the first material of the tip element along a length thereof and a first portion of said laser light energy input is emitted from said curved end face in a focused manner forwardly of said distal end of the tip element.

2. The heating device according to claim 1, wherein:
said first material is selected from a group of laser light transmitting materials such as YAG, sapphire and silica.

3. The heating device according to claim 2, wherein:
a second portion of said laser light energy input is transmitted from a portion of said long side face adjacent said distal end, substantially in a direction transversely of the direction in which said first portion of said laser light energy is emitted from said curved end face.

4. The heating device according to claim 1, wherein:
a second portion of said laser light energy input is transmitted from a portion of said long side face adjacent said distal end, substantially in a direction transversely of the direction in which said first portion of said laser light energy is emitted from said curved end face.

5. The heating device according to claim 4, wherein:
said first portion of laser light energy, emitted from said curved end face, is greater than said second portion of laser light energy.

6. The heating device according to claim 1, further comprising:
a selected high temperature melting point material, incorporated to a predetermined depth into said curved end face and into immediately adjacent predetermined portions of said pair of outer faces and of said long side face, to absorb all laser light energy received thereat through the first material of said tip element.

7. The heating device according to claim 6, wherein:
said high temperature melting point material is selected from a group of materials consisting of titanium, chromium, nickel, zirconium, molybdenum, tantalum, tungsten, yttria, zirconia and alumina.

8. The heating device according to claim 6, wherein:
said high temperature melting point material is incorporated into said first material of the tip element by an ion beam mixing process.

9. The heating device according to claim 6, wherein:
said high temperature melting point material, incorporated into said first material of the tip element by an ion beam mixing process.

10. The heating device according to claims 8 or 9, wherein:
said high temperature melting point material is incorporated into said first material of the tip element forms a secure ballistically alloyed layer extending to a predetermined depth into said first material of said tip element.

11. The heating device according to claim 10, wherein:
said additional layer has a thickness in the range 5,000 Å to 200,000 Å.

12. The heating device according to claim 10, wherein:
said tip element, where said high temperature melting point material is ballistically alloyed into said first material, has a smooth, non-porous external surface.

13. The heating device according to claim 10, wherein:
said high temperature melting point material is selected from a group of materials consisting of titanium, chromium, nickel, zirconium, molybdenum, tantalum, tungsten, yttria, zirconia and alumina.

14. The heating device according to claim 10, further comprising:
an additional layer of the high temperature melting point material, formed to be contiguously bonded to the ballistically alloyed layer.

15. The heating device according to claim 14, wherein:
said high temperature melting point material is selected from a group of materials consisting of titanium, chromium, nickel, zirconium, molybdenum, tantalum, tungsten, yttria, zirconia and alumina.

16. A heating element for use in a device powered by laser light energy, comprising:
a laser energy delivery tip element formed of a laser light transmitting first material, said tip element being defined by a pair of planar parallel elongate outer faces both of same shape and size, a planar proximal end face normal to said pair of outer faces, a first rectangular piecewise continuous planar smooth narrow side face normal to said pair of outer faces and having a substantial elongate first portion normal to the proximal end face, a second rectangular smooth planar narrow side face oriented parallel to said first portion of said first side face, and an at least partially curved distal end face contiguous with said second side face at a distal end thereof and intersecting a second portion of said first side face at a blunt distal end of the tip element; and a high temperature melting point material incorporated into a surface portion of a heating region of the tip element.

17. The heating element according to claim 10, wherein:
said high temperature melting point material is incorporated into said first material of the tip element by an ion beam mixing process.

18. The heating element according to claim 16, wherein:
said high temperature melting point material is incorporated into said first material of the tip element by an ion beam enhanced deposition process.

19. The heating element according to claim 16, wherein:
said surface of said heating region comprises generally quadrantal distal end portions of said elongate outer faces, said quadrantal portions being defined by intersections between distal end portions of the elongate outer faces and said curved distal end face.

20. The heating element according to claim 16, wherein:
said high temperature melting point material is incorporated into the material of the tip element to a first predetermined depth sufficient to totally absorb all laser light energy conveyed thereto through the material of the tip element, whereby all the absorbed laser light energy is converted into heat.

21. The heating element according to claim 20, wherein:
   said first predetermined depth is in the range 20 Å to 5,000 Å.

22. The heating element according to claim 16, 17 or 18, wherein:
   said high temperature melting point material, incorporated into said first material of said tip element forms a securely bonded ballistically alloyed layer extending to a predetermined depth into said first material of said tip element.

23. The heating element according to claim 22, wherein:
   said tip element, where said high temperature melting point material is ballistically alloyed into said first material, has a smooth, non-porous external surface.

24. The heating device according to claim 22, wherein:
   said high temperature melting point material is selected from a group of materials consisting of titanium, chromium, nickel, zirconium, molybdenum, tantalum, tungsten, yttria, zirconia and alumina.

25. The heating element according to claim 22, further comprising:
   an additional layer of the high temperature melting point material, formed to be contiguously bonded to the ballistically alloyed layer.

26. The heating element according to claim 25, wherein:
   said additional layer has a thickness in the range 5,000 Å to 200,000 Å.

27. The heating element according to claim 16, wherein:
   a portion of said curved side face adjacent said second side face contiguous therewith is coated with a reflective layer to ensure internal reflection of laser light reaching the curved side face through the tip element material toward said high temperature melting point material incorporated into the tip element.

28. The heating element according to claim 16, wherein:
   said at least partially curved distal end face is contiguous with said second side face at one end and is contiguous with a planar distal end face normal to said pair of planar elongate outer faces, said elongate outer faces being correspondingly shaped to include distal end surface portions comprising quantrantal and triangular portions; and
   said first narrow side face has an angled planar distal end portion corresponding to and defining said triangular portions in conjunction with said distal planar end face.

29. The heating device according to claim 1, 6, 16 or 27, wherein:
   the tip element is free of sharp cutting edges.

30. The heating device according to claim 1, 6, 16 or 27, wherein:
   an interface between said tip element and said laser light energy input means is located closer to one of said long side face and said short side face than to the other of said side faces.

* * * * *